United States Patent
Behl et al.

(10) Patent No.: US 7,083,779 B2
(45) Date of Patent: Aug. 1, 2006

(54) NONTOXIC DENTAL CARE HERBAL FORMULATION FOR PREVENTING DENTAL PLAQUE AND GINGIVITIS

(75) Inventors: Hari Mohan Behl, Uttar Pradesh (IN); Om Prakash Sidhu, Uttar Pradesh (IN); Shanta Mehrotra, Uttar Pradesh (IN); Palpu Pushpangadan, Uttar Pradesh (IN); Saimbi Charanjit Singh, Uttar Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 12 days.

(21) Appl. No.: 10/397,967

(22) Filed: Mar. 26, 2003

(65) Prior Publication Data

US 2004/0191337 A1    Sep. 30, 2004

(51) Int. Cl.
*A61K 8/97* (2006.01)
*A01N 65/00* (2006.01)

(52) U.S. Cl. .................. 424/58; 424/761; 424/773; 424/775; 424/778

(58) Field of Classification Search .......... 424/58, 424/761, 773, 775, 778
See application file for complete search history.

(56) References Cited

U.S. PATENT DOCUMENTS

| | | | |
|---|---|---|---|
| 4,223,003 A * | 9/1980 | Scheller | 424/9.7 |
| 4,515,785 A | 5/1985 | Shimizu et al. | |
| 4,537,774 A * | 8/1985 | Shimizu et al. | 424/761 |
| 5,009,886 A * | 4/1991 | Ahmad et al. | 424/58 |
| 5,298,251 A | 3/1994 | Locke et al. | |
| 5,371,254 A | 12/1994 | Lidert | |
| 5,466,460 A | 11/1995 | McMahon et al. | |
| 5,472,684 A | 12/1995 | Nabi et al. | |
| 5,484,587 A | 1/1996 | Branly et al. | |
| 5,824,291 A | 10/1998 | Howard | |
| 5,906,825 A | 5/1999 | Seabrook, Jr. et al. | |
| 5,925,356 A | 7/1999 | Subbiah | |
| 5,939,049 A | 8/1999 | Miller et al. | |
| 5,989,604 A | 11/1999 | Wolf et al. | |
| 6,159,508 A | 12/2000 | Wolf et al. | |
| 6,228,402 B1 * | 5/2001 | Wolf et al. | 426/94 |
| 6,264,926 B1 * | 7/2001 | Farooqi et al. | 424/58 |
| 6,274,555 B1 | 8/2001 | Berdami | |

2002/0110600 A1    8/2002    Voorhees et al.

OTHER PUBLICATIONS

Baehni, et al. Oral Diseases, (2003), 9, Suppl. 1, 23-9. (ABSTRACT).*
DuPont, "Prevention of Periodontal Disease", Veterinary Clinics of North America. Small Animal Practice, (Sep. 1998), 28(5) 1129-45.*
Killoy, "Local Delivery of Antimicrobials: A New Era in the Treatment of Adult Periodontitis", Compendium of Continuing Education in Dentistry (Jamesburg, N.J.:1995), (1999) 20 (4 suppl) 13-8; quiz 34-5.*
Westfelt, "Rationale of Mechanical Plaque Control", J. Clin. Periodontol., 1996; 23: 263-267.*
Chopra R.N., Nayar S.L., Chopra I.C. 1956. Glossary of Indian Medicinal Plants, C.S.I.R. Publication, New Delhi, India, 1956.
Gawarikar R., Mehta B.K., Indian Journal of Chemistry, Sep. 1994, 33B:897-898.
Okpanyl S.N., Ezeukwu G.C., 1981, Planta Medica 41:34-39.
Wealth of India. 1994, vol. 3, pp. 596-599 (1994).
Pillai N.R. et al., Anti-Arthritic and Anti-Inflammatory Actions of Nimbidin, Planta Medica 43:59 (1981).
Jarvis A.P. et al., Analysis of Small Samples of Limonoids of Neem (*Azadirachta indica*) using Solid Phase Extraction from Tissue Culture, Phylochemical Analysis 11:184-189 (2000).
Nmila R. et al., Insulinotropic Effect of *Citrullus colocynthis* Fruit Extracts, Planta Medica 66 (2000) 418-423.
Maatooq G.T. et al., 1997, Phytochemistry, 44:187-190.
Darwish-Sayed M. et al., The Glycosidal Content of the Different Organs of *Citrullus colocynthis*, Planta Medica vol. 26, 1974.

* cited by examiner

Primary Examiner—Raymond J. Henley, III
(74) Attorney, Agent, or Firm—Darby & Darby

(57) ABSTRACT

The present invention relates to a synergistic herbal formulation comprising an active fraction from *Azadirachta indica* designated as Fraction A and a fraction from *Citrullus colocynthis* designated as Fraction B, along with a fraction C containing an antioxidant from *Cucumis sativus* extract; and pharmaceutically accepted a carrier wherein the ratio of the components ranging between about 2 to 5.5% of fraction A; about 0.5 to 2.5% of fraction B; about 0.1–0.4% of extract of *Cucumis sativus*; and about 82–97% of carrier or additive.

20 Claims, 5 Drawing Sheets

Figure 3A. Antibacterial activiy of fraction A

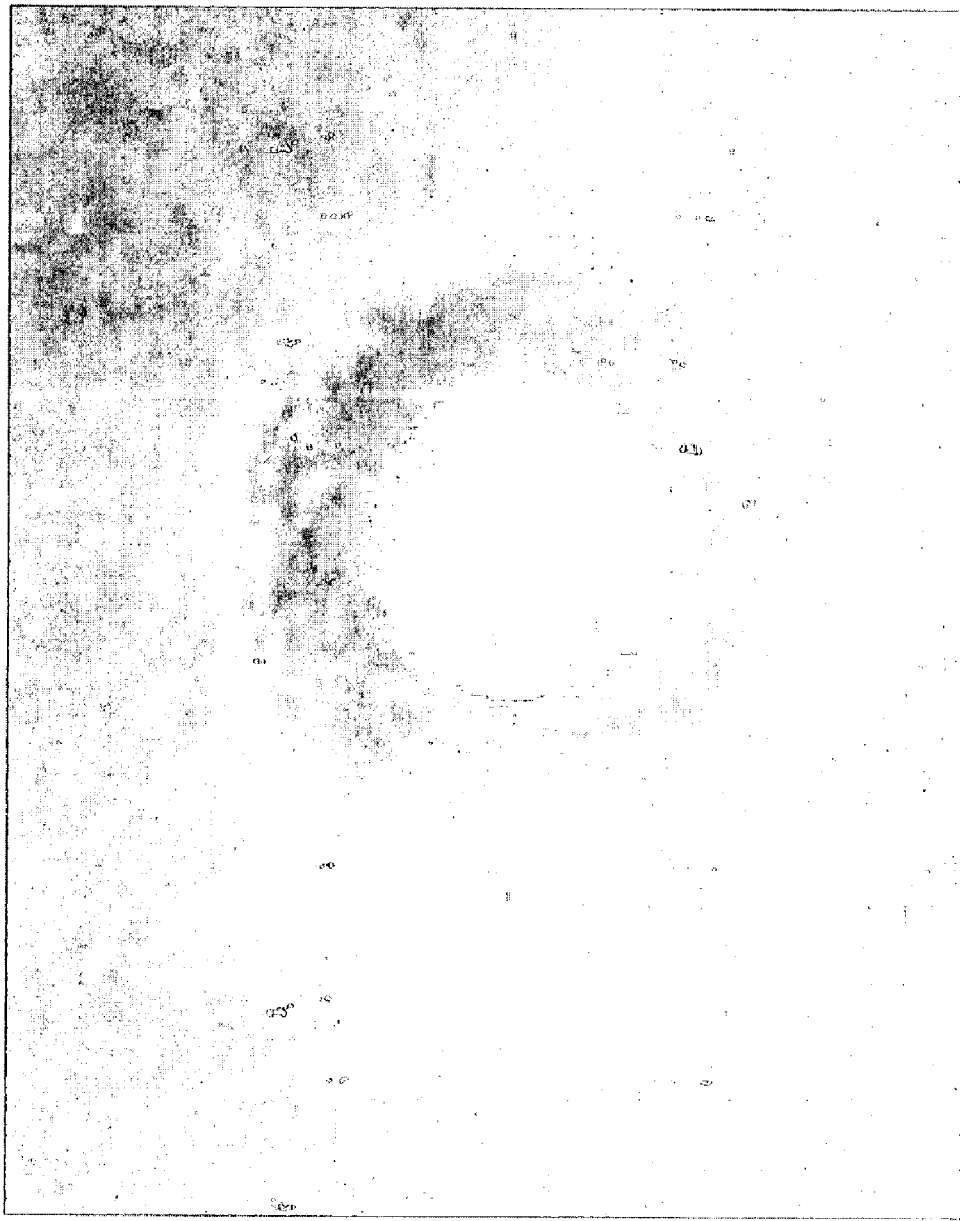
Figure 3B. Antibacterial activity of fraction B

Figure 3C. Antibacterial activity of combination of fraction A and B.

NONTOXIC DENTAL CARE HERBAL FORMULATION FOR PREVENTING DENTAL PLAQUE AND GINGIVITIS

FIELD OF THE INVENTION

The present invention relates to a dental care herbal formulation, its preparation, and its application for control of dental plaque and gingivitis, comprises a combination of active fractions from *Citrullus colocynthis* and neem. The invention includes a process to extract an active constituent of neem bark and leaves as component A, underground plant parts of *Citrullus colocynthis* as component B, and an antioxidant fraction from *Cucumis sativus* as component C. The invention includes an alternative and effective method of extraction of neem leaf and bark by super critical fluid extraction using $CO_2$ as carrier gas for extraction; and further partitioning by liquid phase extraction using a polar and non polar solvent; polar fraction containing nimbolides rich concentrate as component A. The invention includes a process combining component A from neem leaf and bark that comprises primarily nimbolides (2 to 5.5%); component B from *Citrullus colocynthis*, comprising primarily glycosides (0.5 to 2.5%); and addition of 0.1 to 0.4% of antioxidant fraction from component C. Component C has been added to Component A and B to provide antioxidant properties and stability. The objective of this invention is to provide a recipe to develop a dental care formulation combining root of *Citrullus colocynthis*, leaf and bark of neem with an addition of antioxidant fraction from fruits of *Cucumis sativus*.

BACKGROUND OF INVENTION

Herbal medicines or herbal drugs are of ancient origin and their use is known in cultures throughout the world. In India science of herbal medicine known as "ayurveda" medicine, which gives us the modern term "ayurvedic," derived from "ayur," meaning life and "veda" meaning knowledge. A movement to identify individual active ingredients in beneficial herbs developed in the 18th century, leading into a transitional period from the use of natural herbs to the use of pharmaceutical drugs such as extracts and purified chemicals, sometimes referred to as allopathic drugs. With advances in chemistry, some of the active ingredients were chemically synthesized and given to patients in the form of pills. However, during this time of transition, the synthesized, purified or extracted active ingredients of pharmaceutical drugs were observed to exhibit significant adverse side effects.

Generally, herbal medicines do not produce significant side effects, perhaps because the active ingredients are combined with other compounds in the herb and administered in different dosages. In addition, herbs often are administered in combinations, which may nullify the side effect of any one herb. However, purified pharmaceutical drugs seldom are administered in combinations to offset each other's side effects, perhaps because even the offsetting drug is likely to produce its own side effects. It appears that modern medical practice accepts the presence of side effects as an adjunct to the improved purity and efficacy of pharmaceutical drugs. Modern drug synthesis has the advantages of providing pure and potent drugs in large quantities and with considerable speed for wide availability. However, the accompanying problem of side effects is gaining increased notice as the public justly criticizes that such pure and potent drugs can cure one ailment while causing another.

Several plants species are known to have helped in cure, treatment of periodontal diseases, particularly in alleviation of tooth aches. In the literature, several plants have been referred to as commonly used plants for dental care. In recent years, on account of adverse effects of synthetic drugs, attempts have been made upon the potential of phytochemicals for the prevention and treatment of periodontal diseases. Various plant preparations like *Azadirachta indica* (1), *Acacia* (2), Oolong tea (3), *Juglans regia* (4, 5), *Zanthoxylum alantum* (5), *Mimusops elengi* (5) and *Hibiscus abelmoschus* (5) etc. have been used for the prevention of periodontal diseases.

There have been several reviews on neem, however most of these relate to its pesticidal properties (6–8). Almost every part of the tree has long been used in traditional folklore medicines for the treatments of a variety of human ailments, particularly against diseases of bacterial and fungal origin. Antibacterial and antifungal (9) anti-malarial (10, 11), antipyretic and anti-inflammatory (12) are the most frequently cited uses of neem.

Andrew et al. (13) reported that neem is a part of Ayurvedic and folk medicine in India and has a potential for several remedies. Gahukar (14) reported use of neem twigs for pyorrhoea infection. Wolinsky et al (15) investigated bactericidal properties of neem extract.

Their studies with aqueous extracts revealed that bacterial properties are altered and ability of *Streptococci* to colonize tooth surface are inhibited. Farooqi et al. (16) reported that *Azadirachta indica* stem are used as chewing sticks. Guhabakshi et al. (17) reported that different parts of neem (*Azadirachta indica*) such as young branches are used as tooth brushes, particularly in pyorrhoea; and decoction of leaves for washing septic wounds, etc. African members of the Meliaceae such as the Crabwood or Monkey Cola Tree (*Carapa procera*) and Dry Zone Mahogany (*Khaya senegalensis*) are also used as chewing-sticks, and like neem are used to heal (particularly skin and oral infections) and treat malaria (18, 19).

Effect of chewing sticks of neem on dental health has been attributed to presence of fluorides in plants parts. Chawala (20) reported that 20% w/v aqueous extracts of a neem chewing-stick (presence of bark unknown) yielded 2.8 ppm fluoride. Presence of fluoride has been reported to prevent accumulation of bacteria on teeth.

Chewing sticks of *Azadirachta indica* and *Salvadora persica* ("Miswak") were tested for their antimicrobial activity using various concentrations. Both the chewing sticks were effective against *Streptococcus mutans*, and *S. faecalis* (21) Arak extract was more effective at lower concentrations against *S. faecalis*. This difference was attributed to the difference in their pH values.

Neem bark contains tannins and 8 to 11 percent of anti-inflammatory polysaccharides (Terumo Corporation, U.S. Pat. No. 4,515,785). These polysaccharides contain glucose, arabinose and fructose in an approximate ratio of 1:1:1. Apart from these several diterpenoids (Nimbosodione; Nimbisonol; Demethyl Nimbiolon; Margosone; Margosolone; Nimbonone; Nimbonolone; Nimbionone; Nimbionol; Nimbione; Nimbinone and C-seco tetranortriterpenoids isonimbionlide) have also been reported.

Masaki Shimizu et al. (22) patented a process to extract neem bark using solvents like benzene and toluene, etc. The extract was found to retard growth of sarcoma tumours in mice. However, later they extended the patent by reporting extraction in alcohol after treating bark with water at 0° to 40° C.

In 1966 there were only three known triterpenoids from neem. Studies of Jarvis and Morgan (23) on the antifeedant properties in neem seeds led to azadirachtin stimulated research, so that many other compounds were isolated in the 1970's and 1980's from neem (24). Today there are more than 145 known neem triterpenoids, and there must be others yet to be discovered. Little more than one third of these have been tested for biological properties. Many of these triterpenoids (25, 26) have been isolated from neem oil.

Four neem limonoids: gedunin, dihydrogedunin nimbinin, and nimbolide reportedly possess $LC_{50}$ values of 0.72 to 1.74 µg/ml against *P. falciparum* in vitro (27). Some rural communities in Kenya are already using neem for alternate preventive and curative treatment against malaria. A survey of communities in Western Kenya, bordering Lake Victoria, revealed that 98% members of the communities knew about neem; 36% had actually used neem for malaria prevention and treatment (28). They got relief by using bark or leaves boiled in water; some used seed powder dissolved in warm water, or a mixture of neem leaves, bark, and roots boiled in water. These preparations were administered at 1 to 2 glasses twice or thrice a day until recovery as few chewed neem leaves several times a day; other inhaled neem leaf smoke thrice a day.

Use of neem oil is becoming popular for treating ringworm (*Tinea* species) among children in rural Kenya (29). Application of a paste made from neem leaves and turmeric in 4:1 proportion to the skin reportedly cured 97% of the patients suffering from scabies caused by the itch mite, *Sarcoptes scabei* in 3–15 d (30). In Kenya, severe cases of scabies in children are getting cured by bathing with water from boiled leaves and then applying neem oil on affected body parts (29).

Voorhees J. & Nachman L. used 5 to 10% neem leaf powder along with 80 to 88% olive leaf extract and homeopathic blend for preparing a composition for treating symptoms of influenza (U.S. Pat. No. 6,455,070 (Publication No. 2002/0110600).

Wolf et al. (U.S. Pat. No. 6,228,402) have reported a Xylitol containing non-human food stuff for a treatment for reducing the incidence of dental carries in animals (31). They have (not as a claim) but as a suggestion reported that other ingredients including neem oil can be used.

U.S. patent application Ser. No. 07/456,762 and U.S. Pat. No. 5,298,251 (Locke et al.) teach that non-polar hydrophobic solvent extracts of ground neem seed yield a neem oil product that can have combined insecticidal and fungicidal activities. They reported that clarified neem oil demonstrates increased insect repellence, decreased phyto-toxicity, decreased skin irritability, increased fungicidal activity and increased wetting ability. The neem wax demonstrates increased insect repellence, increased fungicidal activity and increased wetting ability (32).

There have been several other patents on neem but these are primarily on use of neem as pesticide or neem based pesticidal stable formulations such as U.S. Pat. No. 4,556,562 (Stable anti-pest neem seed extract); U.S. Pat. No. 4,902,713 (azadirachtin like compound and insect destroyed agents); U.S. Pat. No. 4,943,434 (insecticidal hydrogenated neem extract); U.S. Pat. No. 4,946,681 (method to prepare in improved storage stable neem seed extract); U.S. Pat. No. 4,960,791 (salanin derivation insect control agents); U.S. Pat. No. 5,001,146 (storage stable azadirachtin formulation); U.S. Pat. No. 5,001,149 (azadirachtin derivative insecticides); U.S. Pat. No. 5,047,242 (azadirachtin derivative insecticides); U.S. Pat. No. 5,110,591 (neem oil emulsifier); U.S. Pat. No. 5,124,49 (storage stable azadirachtin formulations); and U.S. Pat. No. 0,436,257 (method of controlling fungi on plants by the aid of hydrophobic extracted neem oil).

*Citrullus colocynthis* Schrad, a member of family Cucurbitaceae, commonly known as "indrayan", "tumba", "Ghorumba", "kaur-tumba", "tumba", "tumbi" or bitter apple is a wild plant. It has also been referred by its earlier name *Citrullus vulgaris*. Colocynth is most abundant in northwestern plains of India, especially in the Barmer, Bikaner, Jaisalmer and Jodhpur districts of Rajasthan, and in Gujarat where it forms large patches on sand dunes, sandy undulating plains and inter-dunal areas; occurs wild throughout India particularly in the Northwest, Central and South India and on the sea shores of the Coromandal coast, Gujarat, and other parts of Western India. In recent years colocynth has found a place in the oil industry of western Rajasthan. Thus, its cultivation in Rajasthan serves three purposes, viz. continuous supply of seed (as cash crop) to oil industry for soap-making; stabilization of shifting sand, and checking the danger of its becoming extinct due to over exploitation.

The fruits and seeds are occasionally used as food in parts of Africa. The gourds are eaten after pickling which makes them safe for eating. They are made into preserves after boiling thoroughly in water to remove their bitterness. They are also used as vegetable after removing their rind. The stem and leaves are eaten by goats and wild game (33–36). Its fruits and seeds have purgative properties, while roots are used as purgatives, used in ascites, jaundice, urinary diseases and rheumatism. These are also used against snake poison. The bitter substance has been reported to be colocynthin and colocynthetin (Amer. J. Pharm., 1893, 179; Pharm. J., 1907, 117; Arch. Harm., Berl., 1883, 201; J. Chem. Soc., 1910, 99; Indian J. med. Res., 1929, 770); roots contain alpha-elaterin, hentria-contane, and saponins (Curr. Sci., 1934, 350); and seeds contain fixed oil, a phytosterolin, phytosterols, hydroxyl carbons, saponins, glycosides and tannin (J. Indian chem. Soc., 1949, 515, 519); pulp contains alpha-elaterin, hentriacontane, a phytosterol and a mixture of fatty acids (B.P.C. 1934, 348) (37–41).

Okieimen et al. (42) reported removal of heavy ions from aqueous solution with melon (*Citrullus vulgaris*) seed husks (Biological Wastes: 0269, 7483, 1989). *Citrullus vulgaris* Schrad has been proposed as an effective feeding stimulant (U.S. Pat. No. 5,968,541). *Citrullus colocynthis* has been used, as a powder, to impart bitter flavour to the composition for topical animal medication such as to prevent common house pets such as dogs and cats from licking their wounds. The claim made in the patent is for use only as a bittering agent (U.S. Pat. No. 6,274,555).

*Citrullus colocynthis* contains several bitter principals; cucurbitacin is one of the major ones present in several genera of the family Cucurbitaceae. The cucurbitacin are a group of bitter-tasting, highly oxygenated, mainly tetra cyclic, triterpenic plant substances derived from the cucurbitane skeleton (43). These compounds are present in many plants and function as an allomone to protect the plants from herbivores (44). In addition, the cucurbitacins are known to have purgative, anti-inflammatory, anti-fungal, and anti-cancer properties (45); and anticancer agents based on natural product models (46).

Commercialization of cucurbitacin-based products has been very limited because (a) the triterpenes are secreted in very small quantities in cucurbitaceous plants, and (b) the existing procedures involved in obtaining pure cucurbitacin is lengthy and burdensome (47). The difficulties involved in obtaining large quantities of cucurbitacins in the past have discouraged serious pursuit of most potential uses of this triterpenes. McMahon et al. (48) taught controlled-release microcapsules that contain insecticides and other compounds useful in crop management. In one embodiment of the invention, the capsule wall contains an anti-feedant compound comprising cucurbitacin-containing solid particles, powder or dust (48). The preferred cucurbitacin-containing solids used are in the form of dried, ground, gourd roots as described in U.S. Pat. No. 4,880,624.

Branly et al. (49) describes baits for diabroticite beetles containing a feeding stimulant and an insecticide. The feeding stimulant comprises plant tissue containing cucurbitacin, and more specifically comprises dried buffalo gourd root in an amount of 10–100 lb. of ground root per acre. Based on this technology, a cucurbitacin-dependent control method for adult cucumber beetles has reportedly been developed. By lacing cucurbitacin-containing plant tissue with insecticide, the beetles are "tricked" by the feeding-stimulant cucurbitacin into eating the toxins.

Ground root tissue containing cucurbitacin has been used as broadcasted bait capable of killing 99% of the diabroticite beetles consuming it (47, 50). However, it is reported that this form of cucurbitacin is effective in the control of adult beetles only, while much of the damage caused by the diabroticite beetles is caused by the larval form (51). The use of purified cucurbitacins in place of plant tissue is one possible solution to this problem, as purified cucurbitacin has been shown to be an effective feeding stimulant for diabroticite beetles in both adult and larval forms. Unfortunately, there are no products marketed today that utilize purified cucurbitacin.

Berdami; L. A. (52) developed a composition and method for topical animal medication consisting of bacitracin zinc, neomycin, polymycin-B sulfate, and pramoxine hydrochiomide. They used *Citrullus colocynthis* as a bittering agent to impart a bitter flavor to the composition such as to prevent common house pets, such as dogs or cats, from licking their wounds.

Subbiah, V. (53) describes a method of isolating and purifying cucurbitacins from *Cucurbita* species (not *Citrullus colocynthis*). Most of the earlier studies on application of cucurbitacin are from *Cucurbita speciea* and not *Citrullus colocynthis*. However, Hatam et el (54) have isolated cucurbitacin glycosides from *Citrullus colocynthis*.

Main diseases of the teeth include plaque, carries and pyorrhoea. Dental plaque is the main cause of most of the periodontal diseases (55, 56). Plaque control is the only effective method of controlling chronic periodontal diseases. People use mechanical devices to control plaque. These are tooth brush used with tooth paste, abrasive powders, interdental cleaning aids, oral irrigation devices etc. However, these practices have several limitations and the entire tooth surface cannot be cleaned. Moreover, once plaque is deposited in substantial quantities, it is difficult to remove with common mechanical methods. Once plaque is deposited, this leads to other diseases. These mechanical aids are not therapeutic in activity; hence chemotherapeutic agents remain in demand for periodontal diseases.

Prominent among the chemicals used are antibiotics (57), enzymes (58), dextrose (59), chlorhexidine (60), urea peroxide (61), organic and inorganic fluorides (62) and ammonium compounds (63) etc. Many of these products are effective to some extent but either are limited in their use or have side effects. Earlier several plant species have been used for dental care.

Some of plants used as dental care are:

TABLE 1

| # | Name | Activity |
|---|------|----------|
| 1 | *Acacia catechu* | Paste used for Bleeding gums and tooth hypersensitivity |
| 2 | *Acacia nilotica* | Twigs as tooth brush |
| 3 | *Achyrathes aspera* | Twigs as tooth brush |

TABLE 1-continued

| # | Name | Activity |
|---|------|----------|
| 4 | *Azadirachta indica* | Twigs as tooth brush |
| 5 | *Aristolochia bracteolata* | Root juice applied at the site of pain |
| 6 | *Carapa procera* | Twigs as tooth brush; oral infections |
| 7 | *Cinnamomum camphora* | Paste applied or tender twigs chewed |
| 8 | *Cinnamomum verum* | Powdered stem bark is applied to teeth in the treatment of caries and pyorrhea |
| 9 | *Curcuma longa* | Powder of rhizome is used in tooth powder for curing pyorrhea |
| 10 | *Eucalyptus globulus* | Leaf oil used to prevent tooth decay and relief of pain |
| 11 | *Ficus bengalensis* | Aerial root is used as tooth brush and the latex is applied in toothache |
| 12 | *Juglans regia* | Stem bark used in tooth powders for healthy teeth |
| 13 | *Hibiscus abelmoschus* | As paste or powder |
| 14 | *Khaya senegalensis* | Twigs as tooth brush; oral infections |
| 15 | *Madhuca longifolia* | Stem bark used in tooth powders for gum pain and toothaches. |
| 16 | *Mimusops elengi* | Stem bark used in tooth powders for gum pain and toothaches. |
| 17 | *Myristica fragrans* | Fruit paste is applied on teeth to cure dental caries and pyorrhea |
| 18 | *Ocimum sanctum* | Leaves paste used for tooth hypersensitivity |
| 19 | *Oolonga tea* | As tea or mouth wash |
| 20 | *Piper betel* | Leaves paste used for tooth hypersensitivity |
| 21 | *Piper longum* | Fruit powder used against dental carries. |
| 22 | *Piper nigrum* | Fine powder of seeds is applied for tooth ache and pyorrhea and bleeding gums. |
| 23 | *Potentilla fulgens* | Root powder is applied in gingivitis |
| 24 | *Punica granatum* | Stem bark or fruit rind is used in tooth powders. |
| 25 | *Salvadora persica* | Twigs as tooth brush; roots against dental carries. |
| 26 | *Syzygium aromaticum* | Clove oil is applied for toothache, dental caries and pyorrhea |
| 27 | *Spilanthes calva* | Flowers chewed in toothache. |
| 28 | *Zanthoxylum armatum* | Twigs as tooth brush; fruits applied to teeth in toothache. |

These plants have been reported as effective anti-plaque inhibitors without any side effects. Some of the herbal extracts especially neem in "in vitro" studies have also shown inhibition of *Staphylococcus aureus, Streptococcus pyogens* and anaerobes. These "in vitro" studies support the anti plaque potentiality of neem.

Neem has been used as a component of toothpastes, mouthwashes, food compositions gingivitis, for reducing caries and treatment of inflammation of the mouth, as a natural flavoring agent in oral compositions used for treating plaque and gingivitis (64–66).

It has also been used as a component of chewing gum containing a teeth whitening agent (67).

Ahmad, et al. (68) used micro-sized particles or microfibers of branches or roots of plants named by them as *Azadirachta* or Salvadora persica, and commonly known in different parts of the world as the peelu, miswaak, neem or siwak tree. They used these particles in place of commonly used mineral abrasives.

Scheller (69) in his patent (U.S. Pat. No. 4,223,003) used neem oil as one of the optional components of their paste and powder dentifrices.

Miller S. E. and Simone A. J. reported formulation of chewing sticks made from natural fibers. They suggested use of neem oil but no claim to its properties was made. Also no description of extraction of oil or plant parts used was given (70).

Nabi et al (71) reported a formulation comprising thymol and eugenol, and optionally a sesquiterpene alcohol. They claimed the formulation to have plaque and gingivitis effects. They suggested use of neem oil to provide an organoleptically acceptable oral product.

Seabrook, Jr. et al. suggested use of neem seed, leaf, bark extracts and oil in their formulations of polymers containing antimicrobial agents. They suggested that the antimicrobial agents include phytochemicals and phyto-nutrients such as naturally occurring extracts from plants and herbs and other chemical disinfectants (72).

At present, a number of tooth powders which contain cheap pulverized items that are not very effective as well as harmful for gums and teeth and have toxic effects are available in India. Compositions of some of the herbal tooth powders as available in market are given below:

| Product name | Manufacturer | Ingredients |
|---|---|---|
| Red Tooth Powder | Dabur India Ltd., 22, Site IV Sahibabad, Ghaziabad, India | Pudina sativa (*Mentha* sp.), avang ka tail, Tomer beej (*Zanthoxylum acanthopodium*), Kapoor, Kalimarich (*Piper nigrum*), Pippali (*Piper longum*), Sunthi (*Zingiber officinale*), Tambaku (*Nicotiana tabacum*) |
| Vicco Vajradanti | Vicco Laboratories, 25, Jerbi Wadia Road, Parel, Bombay-400012, India | Babbul (*Acacia nilotica*), Janibhul, Lavang (*Syzygium aromaticum*), Manjishtha (*Rubia cordifolia*), Dalchini, (*Cinnamomum zeylanicum*), Vajradanti (*Potentilla fulgens*), Acrod, Khair patang, Akkal Kadha, Babul, Jeshthamadh, Kabachini (*Piper cubaba*), Anant root, (*Hemidesmus indicus*), Ajwain, (*Trachyspernum ammi*), Jaifal, (*Myristica fragrans*), Trifala (*Emblica officinal* is, *Terminalia chabula*, *Terminalia belerica*), rice husk, sugar, alum, salt. |
| Lordent Toothpowder | Lord's Cosmetics International A-21/27, Naraina Industrial Area, Phase-II, New Delhi-110028, India | Extract of Plantago, Calendula and creosote |
| Meghdoot dantusha | Meghdoot Gramodhyog, Seva Sansthan, Meghdoot Building, Chandganj Garden, Lucknow, India | Sonth (*Zingiber officinale*), Seva Sansthan, Pipal (*Ficus religiosa*), Kalimirch (*Piper nigrum*, Tomar beej (*Zanthoxylum acanthopodium*), Samundar Jhag, Akarkara (*Anacyclus pyrethrum*) Manjuphal, Maulshri (*Mimosops elengi*), Sengdha salt. |
| Payorin | Dawakhana Tibbiya, College, AMU, Aligarh | Amla (*Emblica officinalis*), Sokhta, Gile gaimuliya, Taj galmi, Kafoor khlis, Hamize |
| Hamdard Manjan | Hamdard (Wakf) Laboratories, Hamdard Marg, Delhi, India | Ilaichi (*Electtaria cardamomum*) kalan, Amla (*Emblica officinalis*), halaila zard (*Terminalia chebula*), Banslochan, *Bambusa bambos*), Zanjbeel, *Zingiber officinale*), Sangjarahat, Filfil siyah (*Piper nigrum*), Kabab khandan, Khoolanjan (*Alpinia galanga*), Namak Sambhar, Mileh firangi, Sat paudina (*Mentha* spp) |
| MDH Dant powder | Super Delicocies Pvt. Ltd. | Acacia nilotica, Embelia tsjenam-cottam, Areca catechu, Juglans regia, Curcuma amada, Syzygium aromaticum, Alpinia galangal, Ficus elastica, Piper nigrum, Menthol, Eucalyptus oil. |
| Payakil | Gurukul Pharmacy, Haridwar, India | Acacia nilotica, Juglans regia, Camphora officinatum, Azadirachta indica, Arcila vitrolutcum, Zanthoxylum armatum |

Critical Review of Earlier Patents/Prior Art

Data related to clinic value of neem used as chewing sticks are rare and only in generic forms.

Formulations are crudely prepared as aqueous solutions, chewing sticks, or leaf and bark extracts.

Claims are made of effect of azadirachtin (from neem) in formulations; azadirachtins have been reported to have insect antifeedant and repellent properties and there are no claims for dental protection.

Some of the commercial dental care formulations suffer from a number of disadvantages. Some stain teeth and gums. Most of these products lack standardization.

No prior art of use of *Citrullus colocynthis* for dental cure, alone or in combination of *Azadirachta indica*

Majority of patents and formulations (quoted in the text) are on pesticidal activities for filed crop of neem.

Berdami, L. A. (U.S. Pat. No. 6,274,555) used *Citrullus colocynthis* as a bittering agent in their composition for topical animal medication. They used a few grains of *Citrullus colocynthis* as a bittering agent to impart a bitter flavor to the composition such as to prevent common house pets, such as dogs or cats, from licking their wounds. No claim with respect to cure for plaque or gingivitis was made. Moreover they did not use roots of *Citrullus colocynthis*.

Cucurbitacins from *Citrullus* like plants has been used as in U.S. Pat. No. 5,466,460 as an antifeedant compound in the walls of capsules containing targeted insecticide. The use thus is only as an antifeedant.

Locke et al. (U.S. Pat. No. 5,298,251 and U.S. patent application Ser. No. 07/456,762) reported a fungicidal composition derived from neem oil and neem wax fractions. However they did not use neem leaves and bark and no claim to therapeutical use against dental plaque or gingivitis was made.

Seabrook, Jr. et al. (U.S. Pat. No. 5,906,825) suggested use of neem seed, leaf, bark extracts and oil in their formulations of polymers containing antimicrobial agents. They claimed their use as antimicrobial agents, however, neem was suggested as one of several agents; moreover this was only a suggestion and not a component of the claims of the patent. They also did not describe the extraction procedure and no claim or mention of anti-plaque or anti-gingivitis was made.

U.S. Pat. Nos. 4,515,785 and 4,537,774 by Masaki Shimizu et al. (20) where they reported a procedure to extract neem bark using solvents like benzene and toluene, etc. (the extract was found to retard growth of sarcoma tumours in mice) and later extended the same by reporting extraction in alcohol after treating bark with water at 0° to 40° C. for higher purity does not incorporate cold extraction; or any combination with leaves or any other plant. They have also no claim on dental formulations. Their claim is on anti-tumour properties on sarcoma tumours in mice.

U.S. Pat. No. 6,264,926 by Farooqi et al. (16) reported a synergistic composition comprising the pastes or powders of *Zanthoxylum armatum*, Zingiber officinale, Sandalwood, Roasted alum, Common salt, Spilanthes calva, Pistacia sp., *Quercus infectoria*, Usnea longisima in the proportion of 20–25%, 25–30%, 8.25–8.5%, 8–9%, 15–16%, 2–2.5%, 2–2.5%, 8–8.5%, and 1–4% respectively. They did not use either *Azadirachta indica* or *Citrullus colocynthis* in their formulation.

Howard H. S. has used (42x) neem oil in chewing gum containing a teeth whitening agent. The neem oil as described in their patent has been taken from neem seeds (not from leaves and bark). Moreover the oil has been extracted using hexane from neem seeds and not leaves and bark. Also they have made no claims to its therapeutical use. Others such as Lewis W. H. (63); Maurice M. I. (64) and U.S. Pat. Nos. 5,371,254; 5,472,684 and HI 541 have reported its utility for gum diseases yet no details of the proportions to be used, methods of extraction and any synergistic effects with other plants have been detailed.

Ahmad et al. (1991) in U.S. Pat. No. 5,009,886 on Dentifrice used micro-sized particles or microfibers of *Azadirachta indica* or *Salvadora*. It is not clear if they are botanically correct in naming the plants since they have named neem, peelu, miswaak or siwak as synonyms. In the detailed description they have mentioned only pilu which is botanically *Salvadora persica*. Moreover they have used wood for preparing abrasive in their dentifrice.

Schellerin's patent on paste and powder dentifrices (U.S. Pat. No. 4,223,003) used neem oil as one of the optional components, however no claim has been made on the benefit they derived by using neem oil. Moreover they have used neem oil apparently derived from neem seeds and not leaves and bark.

Nabi et al. in U.S. Pat. No. 4,223,003 reported a formulation comprising thymol and eugenol, and optionally a sesquiterpene alcohol. They claimed the formulation to have plaque and gingivitis effects. They used neem oil as a flavouring agent, however it was only one the agents selected from the group consisting of Tulsi oil, Neem oil, Eichinacea tincture, rosemary extracts, golden seed extracts, passion flower extract, turmeric extracts, betel nut extracts, sunphenon tea extracts, and dandelion root extracts. Neem oil was used only as a flavouring agent. No details of preparation of neem oil have been given; apparently, it was oil extracted from seeds and not leaves and bark.

Wolf et al. (U.S. Pat. Nos. 5,989,604 and 6,159,508) suggested use of neem oil in their xylitol based formulation for dogs (non-human animals) for reducing the incidence of dental carries. The invention is based on Xylitol, however as a suggestion they have listed several plants such as gum arabic, beef broth, chicken broth or distilled water, lecithin, Coenzyme Q10, folic acid, aloe vera, comfrey, rosemary, goldenseal, horsetail, arnica, calendula, barley grass, chamomile, bloodroot, siwak-miswak, pullulan, horse chestnut, neem, peelu, propolis, green tea, myrrh, birch bark, white oak bark, tea tree oil, grape seed extract, wheat germ, bromelain, papain and quercetincan be added to promote health of hard and soft dental tissue. There was no claim of the inventors as to use of neem as a cure or protection against dental plaque or gingivitis. This was only suggested as one of the several options to promote health of tissue when added to Xylitol. No method of extraction or details of the plant parts used has been given.

Wolf et al. (U.S. Pat. No. 6,228,402) have reported a xylitol containing non-human food stuff for a treatment for reducing the incidence of dental carries in animals. They have as a suggestion added that other ingredients such as XXX can be added to promote health of hard and soft dental tissue. There was no claim of the inventors as to use of neem as a cure or protection against dental plaque or gingivitis. This was only suggested as one of the several options to promote health of tissue.

OBJECTS OF THE INVENTION

The main objective of the present invention is to provide a herbal formulation useful for periodontal diseases, preventing dental plaque and gingivitis.

Another objective is to provide a formulation with no side effects, and free them from any toxicity or toxic residue and irritation when regularly used and which can give effective protection to teeth. It should be cosmetically acceptable and should not leave stain on teeth or fingers after use.

Yet another objective of the present invention is to provide a formulation which contains natural and medicinal plants useful for gums and teeth, which are safe, nontoxic and biodegradable.

SUMMARY OF THE INVENTION

The invention relates to a synergistic dental care herbal formulation comprising of fractions containing active constituents from neem (*Azadirachta indica*), *Citrullus colocynthis* and a fraction with antioxidants from *Cucumis sativus*. The invention includes a process to combine component A from neem bark and leaf fraction rich in nimbolides; component B from underground part preferably root of *Citrullus colocynthis* comprising primarily glycosides; addition of 0.1 to 0.4% of fraction rich in antioxidants from *Cucumis sativus* as component C and a carrier 5–18% edible grade ethanol. The herbal formulation is useful for preventing and control of dental plaque and gingivitis applying on teeth and gums over a period of two weeks or more. The invention providing herbal formulation is non-toxic and biodegradable, suppressing growth of wide spectrum of micro organisms causing periodontal diseases; and useful in the form of lotion, cream, mouthwash, mouth rinse, toothpaste or similar forms of application in daily life or therapeutical application etc.

The invention includes a process to extracting active constituent (primarily nimbolides) from neem bark and leaf, primarily glycosides from roots of *Citrullus colocynthis* using a polar solvent and non-polar solvent. It includes a process to purify active constituents from the above said fractions by partitioning through liquid phase extraction using a polar and a non polar solvent to obtain desired fractions from neem and *Citrullus colocynthis* as component A and B, respectively.

In a preferred embodiment of the invention, an alternative and effective method of extraction of neem bark and leaf by Super Critical Fluid Extraction using $CO_2$ as carrier gas for extraction; and further partitioning by liquid phase extraction using a polar and a non-polar solvent; the polar fraction with enriched nimbolides as the active constituent (component A).

The invention further includes a process to extract and combine an antioxidant fraction from *Cucumis sativus* by cold extraction using aqueous polar solvents at temperature around 20° C. using tissue homogenizer; concentration of the filtrate provides stabilization to the formulation as component C.

The invention includes, active constituents derived from herbal sources and are thus safe ecofriendly, biodegradable and have no toxicity and side effects.

BRIEF DESCRIPTION OF THE DRAWINGS

FIG. 3: Demonstration of antibacterial activity of "active fraction A" (FIG. 3A), "active fraction B" (FIG. 3B) and "combination of fraction A and B" (FIG. 3C).

DETAILED DESCRIPTION OF THE INVENTION

Figure 1:
FIG. 1: Dental plaque before application of formulation showing plaque formation on teeth (example from a clinical trial).

The invention provides a synergistic herbal formulation comprising active fractions from neem (*Azadirachta indica*) and from *Citrullus colocynthis*, along with antioxidant rich fraction C from *Cucumis sativus* and a carrier in the ratio ranging between about 2 to 5.5% of neem, 0.5 to 2.5% of *Citrullus colocynthis*, and 0.1 to 0.4% of *Cucumis sativus* apart from 82–97% of carrier or additive.

In an embodiment, the invention further provides a herbal formulation from the plant part used is selected from fruits or roots of *Citrullus colocynthis* and bark and leaves (in ratio of 0.5–2.5 to 2–5.5) of neem, respectively.

The invention includes an antioxidant from fruit peels of *Cucumis sativus* in the ratio ranging from about 0.1–0.4%, and a carrier using 82–97% aqueous edible grade ethanol. The plant part used in fraction A is selected from neem bark and leaves. The ratio of neem bark and leaves used for obtaining the fraction ranges from 1 to 2.5 and 2 to 10%, respectively. The plant part used is selected from fruits or roots of *Citrullus colocynthis*. The antioxidant used is from a plant source.

The antioxidant used is from fruit peels of *Cucumis sativus* and ranging from about 0.1–0.4%. The carrier used is 5 to 18% edible grade ethanol in aqueous solution. The above said herbal formulation is useful for application on teeth and gums as mouthwash, applying on teeth and gums with the help of cotton pellets twice daily for two weeks.

The invention includes, a dental care herbal formulation is useful for preventing dental plaque and gingivitis in humans, and useful as antimicrobial agents for preventing periodontal diseases.

The herbal formulation reduces >61% dental plaque; >60% in vitro bacterial colony forming units (CFU); >25% gingivitis over a period of 2 weeks, showing no any cytotoxicity at concentration as proposed in the present invention and is useful in the form of lotion, cream, mouthwash and mouth rinse etc.

The invention providing a process for preparation of formulation comprising about 2 to 5.5% neem; about 0.5 to 2.5% *Citrullus colocynthis*; about 0.1–0.4% of *Cucumis sativus*; and about 82–97% of carrier or additive. Extracting neem bark and leaves using commercial blender at a temperature of 10–25° C., preferably at about 20° C. and in an aqueous solution of polar solvents, exclusion of tannins by liquid phase extraction using a non-polar organic solvent and a polar solvent; further concentrating and partitioning the above fraction by liquid phase extraction using a polar and a non-polar solvent and obtaining nimbolides rich fraction from neem as component A. Extracting underground parts preferably roots of *Citrullus colocynthis*, using a homogenizer at 7000 to 8000 revolution per minute in an aqueous polar solvent, purifying active constituents by concentrating and partitioning through liquid phase extraction using a polar and a non-polar solvent to obtain polar phase resulting in glycosides rich fraction as component B.

The invention includes a process of extracting an antioxidant fraction from a plant source, preferably, *Cucumis sativus* by cold extraction using aqueous polar solvents at temperature ranging from 10–25° C. using a tissue homogenizer, to obtain the polar fraction as component C.

The invention further providing a process of mixing component A from neem, component B from *Citrullus colocynthis*, component C from *Cucumis sativus*, a carrier in a ratio ranging from 2 to 5.5%, 0.5–2.5%, 0.1–0.4%, 82–97%, respectively to obtain a herbal synergistic dental care formulation.

| Neem (*Azadirachta indica*) | 2 to 5.5 percent w/v |
|---|---|
| Tumba (*Citrullus colocynthis*) | 0.5 to 2.5 percent w/v |
| *Cucumis sativus* | 0.1 to 0.4 percent w/v |
| Edible grade ethanol | 5 to 18 percent |
| Water | to make up 100 ml formulation |

The invention providing an alternative and effective method of extraction of neem bark and leaf by super critical fluid extraction using $CO_2$ as carrier gas for extraction; and further portioning by liquid phase extraction using a polar and a nonpolar solvent, polar fraction resulting in nimbolides rich fraction as component A.

The polar solvent used is selected from the group consisting of methanol, ethanol, acetone, water; the non-polar solvents used is selected from the group consisting of hexane, chlorohexane, petroleum ether, chloroform, ethyl acetate, pyridine.

The present invention is more fully illustrated by the following examples, which are set forth to illustrate the present invention and are not to be construed as limiting thereof.

EXAMPLE 1

Extracting neem bark and leaves using commercial blender at a temperature of 10–25° C., preferably at about 20° C. and in an aqueous polar solvent, exclusion of tannins by liquid phase extraction using a non-polar organic solvent and a polar solvent; concentrating and partitioning the above extract obtained from earlier step by liquid phase extraction using a polar and a non-polar solvent and obtaining polar fraction comprising rich in nimbolides as component A.

Extracting plant parts of *Citrullus colocynthis*, preferably underground parts using a homogenizer at 7000 to 8000 revolution per minute in an aqueous polar solvent; purifying active constituents from extract by concentrating and partitioning through liquid phase extraction using a polar and a non-polar solvent to obtain polar phase as component B.

Further analyzing the active fraction using Semi-Prep and Analytical HPLC. Analyses were performed on a Waters liquid chromatograph equipped with a automated gradient controller, a solvent delivery system, a sample injector fitted with a 20 μL loop, a photo diode array (PDA) detector. A μBondapak™ semi-prep and a μBondapak $C_{18}$ analytical columns used for analysis. Mobile phase consisted of an isocratic mixture of acetonitrile-water at a flow rate of 1.5 mL $min^{-1}$.

Extracting anti-oxidant fraction from a plant source, preferably, *Cucumis sativus* by cold extraction using aqueous polar solvents at temperature ranging from 10–25° C. using a tissue homogenizer, to obtain the polar fraction as component C.

Mixing component A from neem comprising about 2 to 5.5%, component B from *Citrullus colocynthis* about 0.5 to 2.5%; component C from *Cucumis sativus* about 0.1 to 0.4%; and about 82–97% of carrier or additive to obtain a herbal synergistic dental care formulation.

One kilogram of dry powder neem bark and leaf (in the proportion of 7:3) yielding 20.5 g of "active fraction A"; one kilogram of dry powder of *Citrullus colocynthis* root yielding 88 g of "active fraction B". The active fraction A from neem, and active fraction B from *Citrullus colocynthis* and an antioxidant fraction C from *Cucumis sativus* mixed to prepare the final formulation in aqueous ethanol.

EXAMPLE 2

In another example of the invention, neem leaf and bark were extracted using Super Critical Fluid Extraction technique to isolate active metabolites. This technique is preferred over the earlier reported in Example 1 since the technique involves use of only $CO_2$ as a carrier (extraction) gas and no solvent is used. It renders the final extraction product very eco-friendly. Higher nimbolides (nearly 17% higher) could be extracted using this technique.

EXAMPLE 3

Laboratory tests were performed to demonstrate antibacterial activity of neem (Fraction A), *Citrullus colocynthis* (Fraction B), and combination of neem plus *Citrullus colocynthis* (Formulation with synergistic effect). Antibacterial activities of "Fraction A"; "Fraction B" and "Formulation" were evaluated separately. "Formulation" provided results of the synergistic effect of the two components. The invention reveals laboratory tests conducted on several pathogenic strains of bacteria as per details given below:

Antibacterial activity of the said extracts against pathogenic bacterial strains e.g. *E. coli* (strain # 1), *Pseudomonas aeruginosa* (strain # 2), *Streptococcus mutans* (strain # 3), *Pseudomonas fluorescens* (strain # 4), *Klebsiella pneumoneae* (strain # 5), *Proteus mirabilis* (strain # 6), *Staphylococus aureus* (strain # 7) was tested and given below. The activity is measured as inhibition zone (reported as diameter of the zone in mm).

EXAMPLE 3.1

Antibacterial Activity of Fraction A (Neem)

| S.No. | Institute of Microbial Technology (C.S.I.R.), Chandigarh, India (bacterial strain number#) | Activity (Inhibition zone mm) |
|---|---|---|
| 1 | # 443 | 1.1 mm |
| 2 | # 741 | 0.8 mm |
| 3 | # 890 | 0.9 mm |
| 4 | # 1749 | — |
| 5 | # 109 | 2.1 mm |
| 6 | # 425 | 2.3 mm |
| 7 | # 96 | 1.9 mm |

IMTEC = Institute of Microbial Technology, (CSIR), Chandigarh, India

EXAMPLE 3.2

Antibacterial Activity of Fraction B (*Citrullus colocynthis*)

| Bacterial Strain | Activity (Inhibition zone mm) |
|---|---|
| 1 | 1.3 mm |
| 2 | 1.9 mm |
| 3 | 3.1 mm |
| 4 | 2.0 mm |

-continued

| Bacterial Strain | Activity (Inhibition zone mm) |
|---|---|
| 5 | 3.5 mm |
| 6 | 1.8 mm |
| 7 | 3.0 mm |

EXAMPLE 3.3

Antibacterial Activity of the Formulation Comprising Mixture of Fractions A and B

| Bacterial Strain | Activity (Inhibition zone mm) |
|---|---|
| 1 | 3.1 mm |
| 2 | 3.0 mm |
| 3 | 4.5 mm |
| 4 | 3.8 mm |
| 5 | 4.3 mm |
| 6 | 4.0 mm |
| 7 | 3.5 mm |

EXAMPLE 4

A total of 60 volunteer subjects (for various treatments) with their age ranging between 18–30 years were selected from the Outpatient Department of Periodontics, Faculty of Dental Sciences, King George's Medical College, Lucknow. The criteria for the selection of subjects were as follows:

(A) Inclusion Criteria

- No missing teeth
- No developmental anomalies
- No cervical abrasion and erosion on the enamel surface
- Subject with grade I, II or III gingivitis in lower anterior region were selected.

(B) Exclusion Criteria

- Medically compromised, emotionally/mentally disturbed and pregnant females
- Those subjects with history of drug induces gingival enlargement, pregnancy gingival enlargement, pubertal gingival enlargement and fibrotic gingival enlargement This study was divided into two phases:

Phase I:

The effectiveness of "Formulation" was clinically assessed against dental plaque. Dental plaque was also collected for "in vitro" study. Particulars of the individual, baseline plaque score and experimental plaque score were recorded on a Performa. Plaque accumulation was recorded using Turesky-Gilmore-Glickman modification (1970) of Quigley-Hein Plaque Index System as follows:

| Score | Criteria |
|---|---|
| 0 | No plaque |
| 1 | Separate flecks of plaque at the cervical margin of tooth |
| 2 | A thin continuous band of plaque (up to one mm) at the cervical margin of the tooth |
| 3 | A band of plaque wider than one mm but covering less than one third of the crown of the tooth |
| 4 | Plaque covering at least one third but less than two thirds of the crown of the tooth |
| 5 | Plaque covering two third or more of the crown of the tooth |

Plaque Collection:

The plaque was collected from the facial and lingual/palatal surfaces of all teeth, except $3^{rd}$ molars, using curettes; and was suspended in 5.0 ml of sterile phosphate buffered saline (PBS) solution in screw capped vial; and transported to laboratory for Colony Forming Units (CFU) analyses.

EXAMPLE 4.1

Efficacy of Fraction A (Neem) on Reduction of Dental Plaque at Different Segments (Anterior, Posterior, Facial, Lingual, Upper and Lower) Using Quigley-Hein Scoring System

| Segment | Average Baseline plaque (score) | Average Experimental plaque (score) | Dental Plaque Reduction (%) |
|---|---|---|---|
| Anterior | 2.82 | 1.45 | 48 |
| Posterior | 3.12 | 1.84 | 41 |
| Facial | 3.89 | 1.92 | 50 |
| Lingual | 2.19 | 1.30 | 40 |
| Upper | 3.0 | 1.85 | 38 |
| Lower | 2.83 | 1.50 | 47 |

EXAMPLE 4.2

Efficacy of Fraction B (*Citrullus colocynthis*) on Reduction of Dental Plaque at Different Segments (Anterior, Posterior, Facial, Lingual, Upper and Lower) Using Quigley-Hein Scoring System

| Segment | Average Baseline plaque (score) | Average Experimental plaque (score) | Dental Plaque Reduction (%) |
|---|---|---|---|
| Anterior | 2.93 | 1.40 | 52 |
| Posterior | 3.13 | 1.81 | 42 |
| Facial | 3.83 | 2.0 | 48 |
| Lingual | 3.12 | 1.74 | 44 |
| Upper | 3.25 | 1.55 | 52 |
| Lower | 2.83 | 1.50 | 47 |

EXAMPLE 4.3

Figure 2:
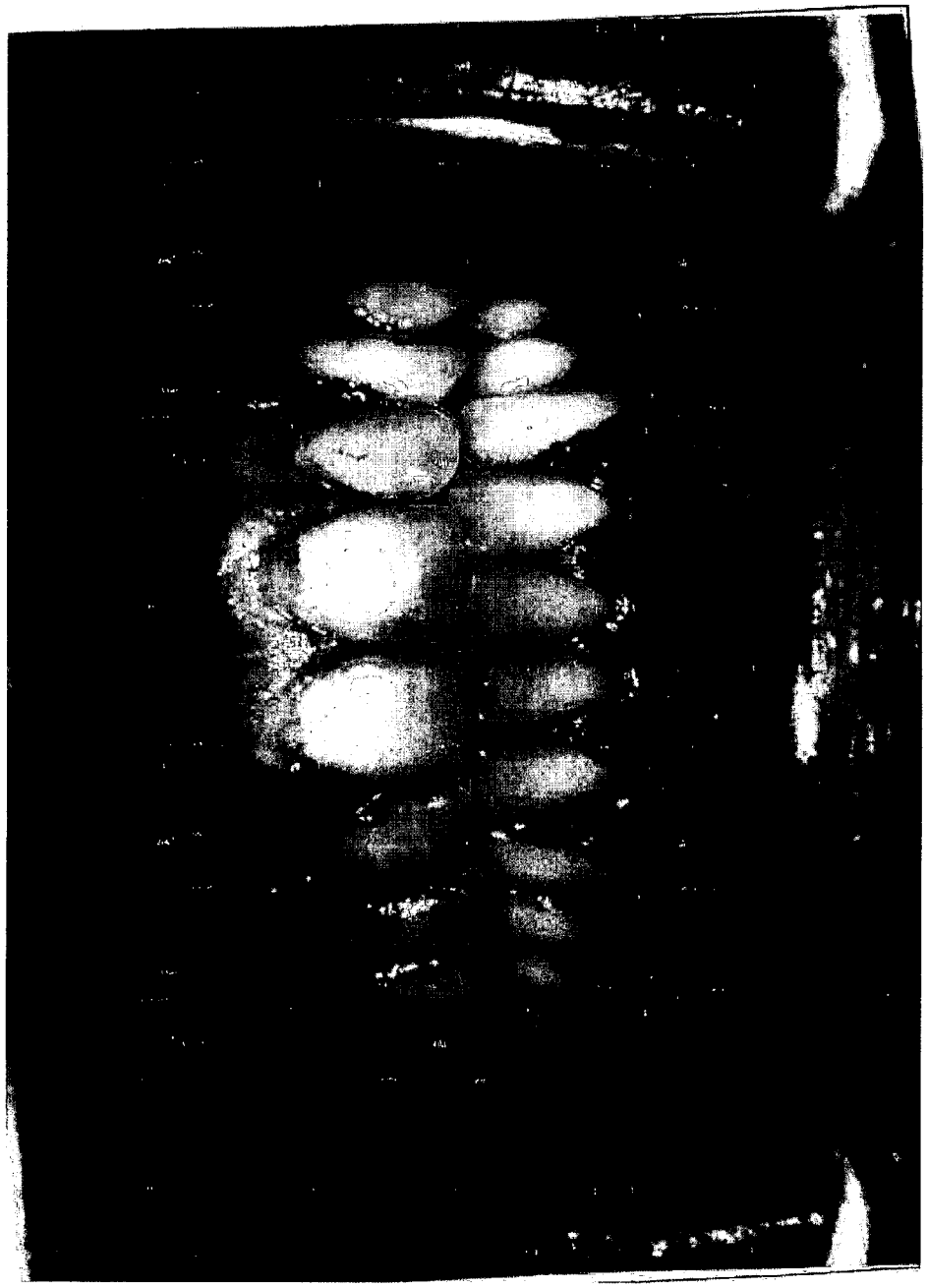
FIG. 2: Controlled dental plaque after application of formulation (example from a clinical trial).

Efficacy of the Herbal Formulation Comprising Mixture of Fractions A and B on Reduction of Dental Plaque at Different Segments (Anterior, Posterior, Facial, Lingual, Upper and Lower) Using Quigley-Hein Scoring System also see FIGS. 1, 2 & 3

| Segment | Average Baseline plaque (score) | Average Experimental plaque (score) | Dental Plaque Reduction (%) |
|---|---|---|---|
| Anterior | 2.92 | 1.04 | 64 |
| Posterior | 3.13 | 1.22 | 61 |
| Facial | 3.89 | 1.18 | 70 |
| Lingual | 2.8 | 1.04 | 63 |
| Upper | 3.25 | 1.18 | 62 |
| Lower | 2.83 | 1.11 | 61 |

EXAMPLE 5

Phase II:

The effectiveness of the *Azadirachta indica* (Fraction A) extracts were tried against different grades of gingivitis.

Thirty subjects with different grade of gingivitis in the lower anterior region were selected. These subjects were divided into three groups each comprising of 10 subjects according to the type of experimental extract used.

Gingival health status was recorded by "Loe and Silness" (1963) gingival index.

The gingival index used is reproduced below:

| Score | Criteria |
|---|---|
| 0 | Normal gingival |
| 1 | Mild inflammation, slight change in colour, slight edema, no bleeding on palpation |
| 2 | Moderate inflammation redness, edema, and glazing, bleeding on probing |
| 3 | Severe inflammation marked redness and edema, ulcerations, tendency to spontaneous bleeding. |

Gingivitis was recorded before starting the clinical trial. After that extract was applied on lower anterior inflamed gingival and the extract was given to the subjects for local application by the patient himself. Patients were advised to apply given extract once in the morning and second time in the evening with the help of cotton pellets for one week. During this period, patients were advised to continue their usual prophylactic procedures. After one week, gingivitis score were recorded on the proforma by the above method. Subjects were advised to apply the same extract for another one week. After second week, gingivitis was again recorded by the same method. The observations were recorded and statistically analyzed.

Efficacy of Fractions A, B and the Synergistic Herbal Formulation Comprising Mixture of A Plus B on Reduction in Gingivitis

| Formulation | Period | Baseline score | Experimental score | Percent reduction |
|---|---|---|---|---|
| Fraction A | 1st week | 2.03 | 2.03 | 0 |
|  | 2nd week | 2.03 | 1.84 | 10 |
| Fraction B | 1st week | 1.90 | 1.88 | 1.05 |
|  | 2nd week | 1.90 | 1.59 | 17 |
| Fraction A + B | 1st week | 2.38 | 2.3 | 3.36 |
|  | 2nd week | 2.38 | 1.77 | 26 |

EXAMPLE 6

Method of Bacterial Enumeration (Total Viable Count)

The total number bacteria in baseline plaque and experimental plaque from subjects were enumerated by spread plate count method in following steps:

a) Diluent Preparation: Phosphate buffered saline (PBS) (Himedia Laboratory Ltd. Mumbai) was dissolved water (9.55 gm/L) and the pH was adjusted 7.2. This solution was autoclaved at 15 lbs/inch$^2$ (121° C.) for 15 minutes and was used as diluent.

b) Preparation of Agar plates: The dehydrated plate count agar medium (Hi Media Laboratories Ltd. Mumbai) was used with following composition:

| | |
|---|---|
| Tryptone | 5 gm/L |
| Yeast extract | 2.5 gm/L |
| Dextrose | 1 gm/L |
| Agar | 15 gm/L |
| And pH | 7 ± 0.2 |

This agar medium was dissolved in distilled water (23.5 gm/L) and boiled in conical flask of sufficient capacity. The flask was cotton plugged and was placed in autoclave for sterilization at 15 lbs/inch$^2$ (121° C.) for 15 minutes. After sterilization, the molten agar in flask was immediately poured (20 ml/plate) into sterile Petri dishes on plane surface. The poured plates were left at room temperature to solidify and incubate at 37° C. overnight to check the sterility of plates. The plates were dried at 50° C. for 30 minutes before use.

c) Preparation of Decimal Dilution: 4.5 ml of PBS was taken in test tube and cotton plugged. These tubes were sterilized by autoclaving. The decimal (ten-fold) dilution was prepared by initiating with 0.5 ml of plaque suspension, which was further processed with other PBS tubes in series for obtaining dilution of 1/10, 1/100, 1/1000 and so on.

d) Inoculation (Plating): The properly marked agar plates were inoculated with 0.1 ml of plaque suspension and their decimal dilutions by using sterile glass pipettes. The inoculum on the agar surface was spread gently up to dryness with a sterile (by dipping in ethanol and flaming) and cooled "L" shaped glass spreader.

e) Plate Counting: All the inoculated agar plates were incubated at 37° C. for 24–48 hours. The number of colonies that appeared on each agar plate was counted and the results were expressed as colony forming unit (CFU)/ml after multiplying with dilution and inoculation factors for each plaque sample. All glassware used were manufactured by Borosil and sterilized in hot air oven at 170° C. for 1 hour.

f) Procedure: At the time of phase 1 clinical trial, oral prophylaxis was performed on all ten subjects and instructed not to clean their teeth by any method for three days. On fourth day, three day old plaque was disclosed by tetrazolium compound disclosing solution. This plaque was considered baseline plaque for each subject and was recorded on a specially designed proforma. After recording and collecting baseline plaque, three days gap was advised to all the subjects. During this period, subjects were advised to continue their routine oral hygiene measures. On seventh day, the plaque score was again reduced to zero in each subject. The test preparation was applied by operator himself with the help of cotton pellets twice daily on the facial and lingual/palatal surfaces of all teeth. After 5 minutes the subjects were asked to rinse with tap water. The procedure was repeated for three days in succession at the end of which plaque score was recorded and collected again. During the test period, subjects were abstained from performing any oral hygiene measure.

All the formulations were tried in each subject by the same method as described above.

Efficacy of Fractions A, B and Mixture of A plus B on In Vitro Colony Forming Units (CFU) of Bacteria Causing Dental Plaque

| Subject # | Reduction percentage of CFU | | |
|---|---|---|---|
| | Azadirachta indica | Citrullus colocynthis | Azadirachta indica + Citrullus colocynthis |
| 1 | 50 | 54 | 59 |
| 2 | 50 | 56 | 57 |
| 3 | 38 | 50 | 63 |
| 4 | 54 | 60 | 67 |
| 5 | 49 | 52 | 60 |
| 6 | 54 | 64 | 65 |
| 7 | 51 | 56 | 60 |
| 8 | 56 | 62 | 65 |
| 9 | 45 | 66 | 68 |

EXAMPLE 7

In another study, the efficacy of the formulation (Mixture of Fractions A and B) was tested in vitro culture experiments. The formulation was compared against Chlorhexidine, Listerine and Betadine, the common mouth wash agents used by periodontal surgeons. Cell viability (toxicology to the cell) was measured. The results revealed that Chlorhexidine, Betadine were cytotoxic even at 0.001%; Listerine was toxic at 10 and 100%; it had potent cytotoxic effects. The formulation as proposed in this invention did not have any cytotoxicity at the concentration used in the invention. The test also revealed that the formulation had a reversible effect on cultured fibroblasts when the cell viability and protein quantification were analyzed. On the other hand Chlorhexidine, Listerine and Betadine damage the cells irreversibly. This supports the contention that the proposed formulation is non-toxic and is safe for use.

ADVANTAGES

The present invention provides several advantages over methods known in the prior art, in that:

The present invention discloses a synergistic herbal formulation comprising an antioxidant from plant source preventing >61% dental plaque and >25% gingivitis applying on teeth and gums over a period of two weeks.

The formulation is safe, non-toxic, biodegradable and without any side effect.

The use of azadirachtin is avoided since this group of compounds has insect antifeedant and repellent properties and poor shelf life when dissolved in water.

Active nimbolide rich fractions with pronounced antibacterial activity has been incorporated in the formulation;

The present invention discloses extraction of fraction containing active glycosides from Citrullus colocynthis;

The present invention allows the practitioner to isolate active fractions from neem and Citrullus colocynthis;

There is a disclosure of invention and application of super critical fluid extracted fraction from neem for dental formulation;

The invention claimed is:

1. A process for the preparation of a formulation comprising 2 to 5.5% w/v (Azadirachta indica from bark and leaves); 0.5 to 2.5% w/v (Citrullus colocynthis); 0.1 to 0.4% w/v (Cucumis sativus): 82–97% w/v of carrier or additive, wherein the said process comprising the steps of:

a. extracting said bark and leaves using a commercial blender at a temperature of 10–25° C., preferably at 20° C. and in an aqueous solution of polar solvents;

b. excluding tannins from the extract of step a by liquid phase extraction using a non-polar organic solvent and a polar solvent;

c. concentrating and partitioning the above extract obtained from step (b) by liquid phase extraction using a polar and a non-polar solvent and obtaining a polar fraction comprising rich in nimbolides as component A;

d. extracting plant parts of Citrullus colocynthis, preferably underground parts, using a homogenizer at 7000 to 8000 revolution per minute in an aqueous polar solvent;

e. purifying the active constituents from above extract in step (d) by concentrating and partitioning through liquid phase extraction using a polar and a non-polar solvent to obtain polar phase as component B;

f. extracting an anti-oxidant fraction from Cucumis sativus by cold extraction using aqueous polar solvents at temperature ranging from 10–25° C. using a tissue homogenizer, to obtain the polar fraction as component C;

g. mixing component A from Azadirachta indica, component B from C. colocynthis, component C from C. sativus, a carrier in a ratio ranging from 2 to 5.5% w/v, 0.5 to 2.5% w/v, 0.1 to 0.4% w/v, and 82–97% w/v respectively to obtaining a herbal synergistic dental care formulation.

2. The process as claimed in claim 1 wherein the polar solvent used is selected from the group consisting of methanol, ethanol, acetone, and water.

3. The process as claimed in claim 1 wherein the non-polar solvents used are selected from the group consisting of hexane, chlorhexane, petroleum ether, chloroform, and ethyl acetate.

4. The process as claimed in claim 1 wherein component A can be alternatively extracted by super critical fluid extraction using $CO_2$ as carrier gas, followed by partitioning of the said fraction by liquid phase extraction using a polar and a non polar solvent, to obtain a polar fraction rich in nimbolides as component A.

5. The process as claimed in claim 4 wherein the non-polar solvents used are selected from the group consisting of hexane, chlorohexane, petroleum ether, chloroform, and ethyl acetate.

6. A process for the preparation of a formulation comprising 2 to 5.5% w/v (*Azadirachta indica* from bark and leaves); 0.5 to 2.5% w/v (*Citrullus colocynthis*); 0.1 to 0.4% w/v (*Cucumis sativus*): 82–97% w/v of carrier or additive, wherein the said process comprising the steps of:
   a. extracting said bark and leaves using a commercial blender at a temperature of 10–25° C., preferably at 20° C. and in an aqueous solution of polar solvents;
   b. excluding tannins from the extract of step a by liquid phase extraction using a non-polar organic solvent and a polar solvent;
   c. concentrating and partitioning the above extract obtained from step (b) by liquid phase extraction using a polar and a non-polar solvent and obtaining a polar fraction comprising rich in nimbolides as component A;
   d. extracting plant parts of *Citrullus colocynthis*, preferably underground parts, using a homogenizer at 7000 to 8000 revolution per minute in an aqueous polar solvent;
   e. purifying the active constituents from above extract in step (d) by concentrating and partitioning through liquid phase extraction using a polar and a non-polar solvent to obtain polar phase as component B;
   f. extracting an anti-oxidant fraction from *Cucumis sativus* by cold extraction using aqueous polar solvents at temperature ranging from 10–25° C. using a tissue homogenizer, to obtain the polar fraction as component C;
   g. mixing component A from *Azadirachta indica*, component B from *C. colocynthis*, component C from *C. sativus*, a carrier in a ratio ranging from 2 to 5.5% w/v, 0.5 to 2.5% w/v, 0.1 to 0.4% w/v, and 82–97% w/v respectively to obtaining a herbal synergistic dental care formulation, wherein the polar solvent used is selected from the group consisting of methanol, ethanol, acetone, and water.

7. A process for the preparation of a formulation comprising 2 to 5.5% w/v (*Azadirachta indica* from bark and leaves); 0.5 to 2.5% w/v (*Citrullus colocynthis*); 0.1 to 0.4% w/v (*Cucumis sativus*): 82–97% w/v of carrier or additive, wherein the said process comprising the steps of:
   a. extracting said bark and leaves using a commercial blender at a temperature of 10–25° C., preferably at 20° C. and in an aqueous solution of polar solvents;
   b. excluding tannins from the extract of step a by liquid phase extraction using a non-polar organic solvent and a polar solvent;
   c. concentrating and partitioning the above extract obtained from step (b) by liquid phase extraction using a polar and a non-polar solvent and obtaining polar fraction comprising rich in nimbolides as component A;
   d. extracting plant parts of *Citrullus colocynthis*, preferably underground parts, using a homogenizer at 7000 to 8000 revolution per minute in an aqueous polar solvent;
   e. purifying the active constituents from above extract in step (d) by concentrating and partitioning through liquid phase extraction using a polar and a non-polar solvent to obtain polar phase as component B;
   f. extracting an anti-oxidant fraction from *Cucumis sativus* by cold extraction using aqueous polar solvents at temperature ranging from 10–25° C. using a tissue homogenizer, to obtain the polar fraction as component C;
   g. mixing component A from *Azadirachta indica*, component B from *C. colocynthis*, component C from *C. sativus*, a carrier in a ratio ranging from 2 to 5.5% w/v, 0.5 to 2.5% w/v, 0.1 to 0.4% w/v, and 82–97% w/v respectively to obtaining a herbal synergistic dental care formulation, wherein the non-polar solvent used is selected from the group consisting of hexane, chlorohexane, petroleum ether, chloroform, and ethyl acetate.

8. A process for the preparation of a formulation comprising 2 to 5.5% w/v (*Azadirachta indica* from bark and leaves); 0.5 to 2.5% w/v (*Citrullus colocynthis*); 0.1 to 0.4% w/v (*Cucumis sativus*): 82–97% w/v of carrier or additive, wherein the said process comprising the steps of:
   a. extracting said bark and leaves using a commercial blender at a temperature of 10–25° C., preferably at 20° C. and in an aqueous solution of polar solvents;
   b. excluding tannins from the extract of step a by liquid phase extraction using a non-polar organic solvent and a polar solvent;
   c. concentrating and partitioning the above extract obtained from step (b) by liquid phase extraction using a polar and a non-polar solvent and obtaining polar fraction comprising rich in nimbolides as component A;
   d. extracting plant parts of *Citrullus colocynthis*, preferably underground parts, using a homogenizer at 7000 to 8000 revolution per minute in an aqueous polar solvent;
   e. purifying the active constituents from above extract in step (d) by concentrating and partitioning through liquid phase extraction using a polar and a non-polar solvent to obtain polar phase as component B;
   f. extracting an anti-oxidant fraction from *Cucumis sativus* by cold extraction using aqueous polar solvents at temperature ranging from 10–25° C. using a tissue homogenizer, to obtain the polar fraction as component C;
   g. mixing component A from *Azadirachta indica*, component B from *C. colocynthis*, component C from *C. sativus*, a carrier in a ratio ranging from 2 to 5.5% w/v, 0.5 to 2.5% w/v, 0.1 to 0.4% w/v, and 82–97% w/v respectively to obtaining a herbal synergistic dental care formulation, wherein the non-polar solvent used is selected from the group consisting of hexane, chlorohexane, petroleum ether, chloroform, and ethyl acetate.

9. A method of treating dental plaque in a human in need thereof wherein the method comprises the application of the formulation produced by the process according to any one of claims 1–8 to said human's teeth and gums, wherein said formulation is a dental care herbal formulation.

10. The method of claim 9, wherein the formulation reduces at least 61% dental plaque over a period of two weeks.

11. A method of treating dental gingivitis in a human in need thereof where the method comprises the application of the formulation produced by the process of any one of claims 1–8 to said human's teeth and gums, wherein said formulation is a dental care herbal formulation.

12. A method of inhibiting periodontal disease in a human in need thereof wherein the method comprises the application of the formulation produced by the process of any one of claims 1–8 to said human's teeth and gums, wherein said formulation is an antimicrobial dental care herbal formulation.

13. A dental care herbal formulation produced by the process according to any one of claims 1–8.

14. The dental care herbal formulation of claim 13, wherein in said process for the preparation thereof, the ratio of bark and leaves of *Azadirachta indica* ranges from 1 to 2.5% and 2 to 10%, respectively.

15. The dental care herbal formulation of claim 13, wherein in said process for the preparation thereof, the *Citrullus colocynthis* of component B is from a plant part selected from the group consisting of the fruit of *Citrullus colocynthis* and the roots of *Citrullus colocynthis*.

16. The dental care herbal formulation of claim 13, wherein in said process for the preparation of said formulation, the antioxidant is obtained from the fruit peels of *Cucumis sativus* and is present in said formulation in a range of from 0.1–0.4% w/v.

17. The dental care herbal formulation of claim 13, wherein in said process for the preparation of the formulation, the carrier used is 5 to 18% w/v edible grade ethanol in an aqueous solution.

18. The dental care herbal formulation of claim 13, wherein said formulation is in the form of a lotion, cream, mouthwash, tooth or gum paste.

19. A method of treating dental plaque and gingivitis, wherein the method comprises application of the herbal formulation as claimed in claim 13, wherein the formulation is applied on teeth and gums, twice daily for two weeks.

20. A method of treating dental plaque and gingivitis, wherein the method comprises application of the herbal formulation as claimed in claim 13, wherein the formulation is applied on teeth and gums in the form of a mouthwash or mouth rinse.

* * * * *